United States Patent [19]

Aeschbach

[11] 4,358,463
[45] Nov. 9, 1982

[54] METHOD FOR THE PRODUCTION OF FERMENTATION VINEGAR

[75] Inventor: Hermann A. Aeschbach, Montreux, Switzerland

[73] Assignee: Process Engineering Company SA, Maennedorf, Switzerland

[21] Appl. No.: 188,277

[22] Filed: Sep. 18, 1980

[30] Foreign Application Priority Data

Sep. 26, 1979 [CH] Switzerland .......................... 8642/79

[51] Int. Cl.$^3$ .............................. C12J 1/04; C12P 7/54
[52] U.S. Cl. ........................................................ 426/17
[58] Field of Search .......................................... 426/17

[56] References Cited

U.S. PATENT DOCUMENTS

| | | | |
|---|---|---|---|
| 928,578 | 7/1909 | Antoni | 426/17 |
| 1,214,518 | 2/1917 | Defren | 426/17 |
| 3,445,245 | 5/1969 | Ebner | 426/17 |
| 4,076,844 | 2/1978 | Ebner | 426/17 |
| 4,282,257 | 8/1981 | Kunimatsu | 426/17 |

FOREIGN PATENT DOCUMENTS 2755528  6/1978  Fed. Rep. of Germany ........ 426/17

*Primary Examiner*—Jeanette M. Hunter
*Attorney, Agent, or Firm*—Michael J. Striker

[57] ABSTRACT

A method for the submersed, automatically controlled production of fermentation vinegar from ethanol is conducted in two stages. The installation for accomplishing the method includes one or more pre-fermenters and a product fermenter, in connection with which each pre-fermenter exhibits a volume 1.7 to 3.5 times that of the product fermenter. The terminus of the fermentation is reached in the product fermenter when the dissolved oxygen, indicated by means of an oxygen electrode, rises, at which point the product valve is opened. The product fermenter is evacuated when no more alcohol remainder is present. In the final step the alcohol is therefore completely utilized.

5 Claims, 1 Drawing Figure

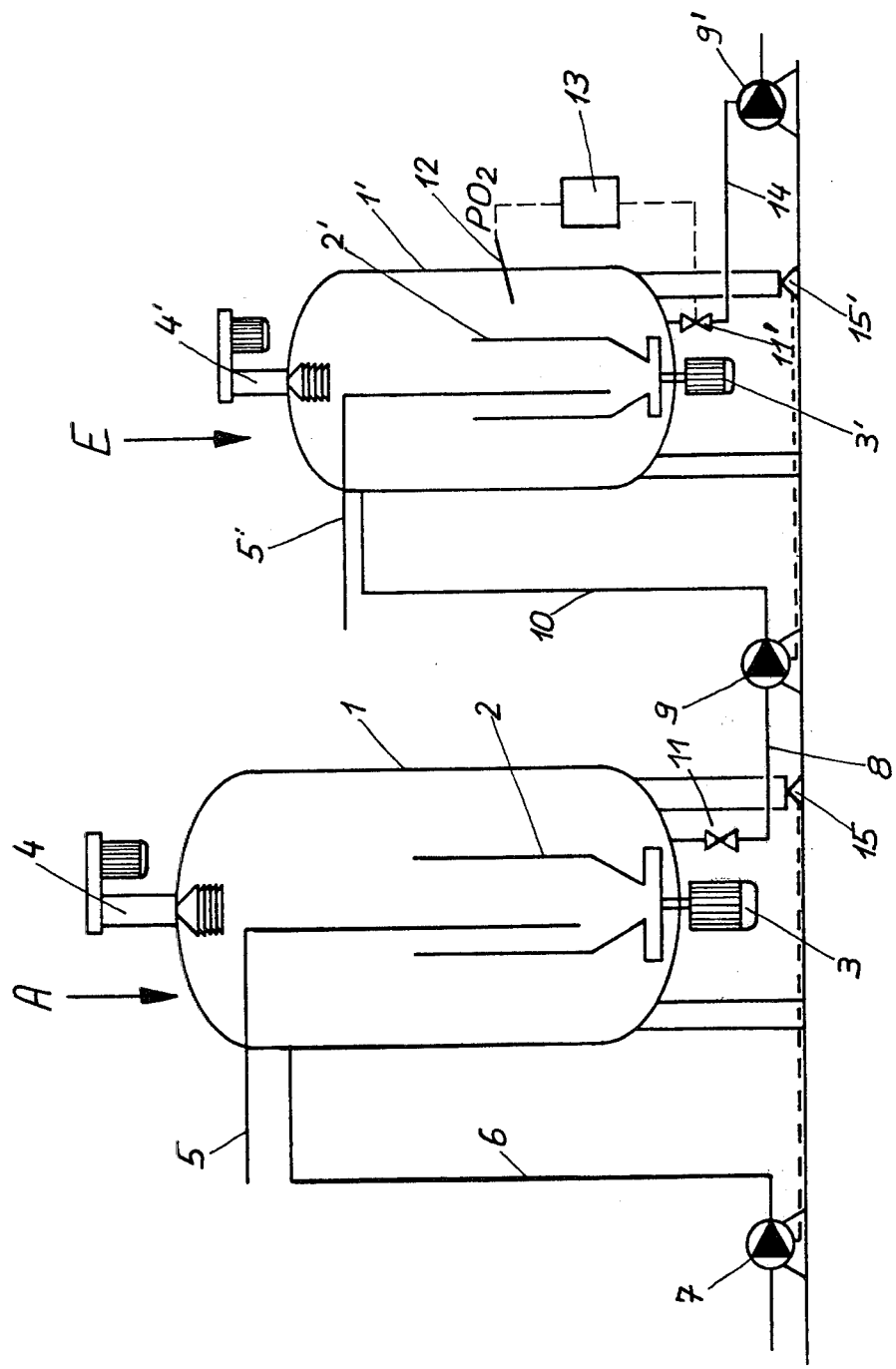

METHOD FOR THE PRODUCTION OF FERMENTATION VINEGAR

BACKGROUND OF THE INVENTION

This invention concerns both a method and an installation for the submersed, automatically controlled production of fermentation vinegar from ethanol.

Production proceeds in two stages, there being one or more of the preliminary stage.

An arrangement for the production of fermentation acetic acid is known from Swiss Pat. No. 375,315, which operates in principle with two refining units of similar capacity. After complete evacuation of one of the vessels, accordingly as all of the alcohol is consumed, it will be inoculated with a portion from the second vessel and refilled with fresh mash. The end point of the acidifying is determined as a function of the subsidence of the temperature of the medium.

Another two-stage method, according to DE-PS No. 26 57 330, supplies an acid concentration above 15% acetic acid, with an alcohol content of less than 0.5%. There, the bacteria multiplication and acidifying are to be conducted in a first fermentation phase. In a second fermentation phase the acidifying along with the introduction of the acetic acid bacteria is practically finished. Acetic acid bacteria do not multiply much and hence produce acetic acid very slowly. This influences the economy of the method.

Further disadvantages of the known processes are that with a controlling of the vinegar ejection with regard to the temperature a process variable is used which can be influenced by outside considerations and not simply according to the microbiological process. An additional disadvantage of the methods mentioned is that the utilization of the alcohol in the finishing fermentation step is incomplete.

SUMMARY OF THE INVENTION

The object of the invention is therefore to accomplish a method whereby the complete utilization of the alcohol changed into acetic acid is automatically controlled, as well as an installation for the conducting of the method.

This object is achieved through a method in which at the terminus of the fermentation the product valve and the product pump of the product fermenter are controlled by means of an oxygen electrode according to the increase of the dissolved oxygen.

In the course of the fermentation the alcohol content continuously decreases in a final step without the introduction of new substrate, while with constant air supply the dissolved oxygen remains constant up to that point at which the alcohol is consumed completely. The partial pressure ($pO_2$) of the dissolved oxygen is measured as control parameter for the determination of the end point of the fermentation. This controls the progress of the fermentation, in doing which the process variable thusly is converted so that a relative value from 0% dissolved oxygen will be adhered to at normal productivity. Complete absorption of the introduced oxygen is thus obtained in this phase. In the end phase a relative value from 100% dissolved oxygen will be obtained, so that complete consumption of the oxidizable alcoholic substrate is signified. The increase of the $pO_2$-process variable will by means of threshold contact with the range of 70–100% be used for release of the control.

The acidifying ensuing up to the final concentration of the biologically oxidizable ethanol practically signifies an alcoholic remainder of zero. The output stage becomes completely depleted except for remaining alcohol. Thereupon the void fermentation container of the output stage is filled again automatically with a volume portion of the substrate together with the acetic acid bacteria from one or more prefermenters, while new mash is introduced into the pre-fermenter(s). The pre-acidifying ensues up to an alcohol content from 0.5 to 3 percent by volume.

The volume ratio of the prefermenter to the final fermenter amounts to about 1.7 to 3.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

In the single FIGURE is shown the arrangement for the simplest case of one pre-fermenter A and one product fermenter E.

DESCRIPTION OF THE PREFERRED EMBODIMENT

The pre-fermenter A has 1.7 to 3.5 times the volume of product fermenter E. The two fermenters consist of a container 1 resp. 1', a central conduit tube 2 resp. 2', a drive 3 resp. 3', and a mechanical foam separator 4 resp. 4'. Both containers are provided with hollow body flow checks for stabilizing the temperature, as well as the air supply system 5 resp. 5'. The pre-fermenter A has a substrate supply line 6 which is connected to the feed pump 7. A delivery conduit 8 with valve 11 leads from pre-fermenter A beyond pump 9 to the entry conduit 10 of fermenter E. Fermenter E is provided with a product valve 11', a conduit 14 and a pump 16. The valve 11' is controlled by the oxygen-electrode 12 above the amplifier arrangement 13. Both fermenters are equipped with pressure cells 15 resp. 15' for measuring the container contents.

During operation pre-fermenter A will, to begin with, be pre-acidified up to an alcohol content from 0.5 to 3 percent by volume in known manner. Following that a volume portion will be exacted out of pre-fermenter A across line element 8 through pump 9 and line element 10 to product fermenter E under constant aeration with an air quantity such as is ventilated into pre-fermenter A of 6 m³ per hour and 1 m³ working volume, and with the regulated temperature held constant. The measured value of the dissolved oxygen contents is 0% and rises to 100% in the final stage. From that moment the new conveyance to end fermenter E will be conducted by means of a standard controlled terminal based upon a temporarily determined function of the actual desired value comparison of the dissolved $pO_2$ data, which cuts off so that there does not occur a build-up until constant $pO_2$—development for the clearing of the product control. In operation of the mentioned control condition the obtained working volume of the corresponding pre-fermenter must be reported as given across the standard terminal, in order that no final fermenter evacuation can, with disturbances, result, before the pre-fermenter has concluded its substrate conveyance. In the range from 70–100% valve 11' opens itself, by means of which the contents of fermenter E are conducted through conduit 14 for additional working.

With the approach having two fermenters, the biological system stabilizes itself automatically with no parameter variations; with three fermenters corrections must be undertaken by parameter variations.

By way of a computational example, the equilibrium between partial renewal in the input stage Va and the final stage Ve is presented:

$V_A; V_E [m^3]$ (1) $V_A = \dfrac{V_E}{1 - KQ}$ $[m^3]$    $KQ$ = concentration quotient $S_{NT}$ = acetic acid after partial renewal (2) $KQ = \dfrac{S_{NT} - S_S}{S_{VT} - S_S}$ $[-]$    $S_{VT}$ = acetic acid before partial renewal $S_S$ = acetic acid in substrate (3) $S_{NT} = S_E - \Delta S \left[\dfrac{kg}{m^3}\right]$    $S_E$ = acetic acid in the final stage apart from the remaining alcohol $\Delta S = S_E - S_{NT}$ (4) $S_{VT} = S_E - \Delta S \dfrac{P_E}{P_A + P_E}$    $P_A, P_E$ = productivity, input stage resp. final stage.

The advantages of this method are thereby seen, that the productivity is greater than the sum of the capacities of equally dimensioned single stage fermenters, since in the batch process of the product step active biomass is introduced. By means of the batch process of the product step the oxidizable alcohol will be utilized completely by the acetobacter.

It will be understood that each of the elements described above, or two or more together, may also find a useful application in other types of fermentation productions differing from the types described above.

While the invention has been illustrated and described as embodied in a method and apparatus for the production of fermentation vinegar, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In a method for the submersed, automatically controlled production of vinegar from ethanol, of the type in which fermenting is begun by pre-acidifying mash with acetic acid bacteria, the improvement comprising completing fermenting with constant dissolved oxygen content while the alcohol in said mash becomes completely consumed, with constant air supply and without introduction of new substrate; and recovering vinegar at the terminus of fermentation, by means of a product valve controlled through an oxygen electrode, according to increase in dissolved oxygen content.

2. Method according to claim 1, wherein said pre-acidifying ensues up to an alcohol content of about 0.5 to 3 percent by volume.

3. A continuous method for the production of vinegar according to claim 1, further comprising after said recovering vinegar at the terminus of fermentation automatically filling the thereby evacuated fermentation vessel with a volume portion of substrate together with acetic acid bacteria from one or more vessels used for said pre-acidifying.

4. Method according to claim 3, further comprising after said automatically filling said evacuated fermentation vessels automatically refilling said one or more vessels used for said pre-acidifying with fresh mash.

5. Method according to claim 4, wherein said filling and said refilling are controlled through a weight measuring system.

* * * * *